United States Patent
Sakamoto

[11] Patent Number: 5,228,430
[45] Date of Patent: Jul. 20, 1993

[54] ELECTRONIC ENDOSCOPE APPARATUS INCLUDING EASY FOCUSING DISTAL END

[75] Inventor: Yutaka Sakamoto, Tokyo, Japan

[73] Assignee: Kabushiki Kaisha Toshiba, Kawasaki, Japan

[21] Appl. No.: 562,855

[22] Filed: Aug. 3, 1990

[30] Foreign Application Priority Data

Aug. 4, 1989 [JP] Japan .................. 1-201370

[51] Int. Cl.⁵ .............................................. A61B 1/00
[52] U.S. Cl. .................................... 128/6; 358/98
[58] Field of Search .................. 128/4, 6; 358/98

[56] References Cited

U.S. PATENT DOCUMENTS

| | | | |
|---|---|---|---|
| 4,491,865 | 1/1985 | Danna et al. | 358/98 |
| 4,677,471 | 6/1987 | Takamura et al, | 128/6 |
| 4,745,471 | 5/1988 | Takamura et al. | 128/6 |
| 4,745,570 | 5/1988 | Yabe et al. | 128/6 |
| 4,777,524 | 10/1988 | Nakajima et al. | 358/98 |
| 4,779,130 | 10/1988 | Yabe | 128/6 |
| 4,867,138 | 9/1989 | Kubota et al. | 128/6 |
| 4,890,159 | 12/1989 | Ogiu | 128/6 |
| 4,918,521 | 4/1990 | Yabe et al. | 128/6 |
| 4,919,114 | 4/1990 | Miyazaki | 358/98 |

*Primary Examiner*—Ralph Lewis
*Attorney, Agent, or Firm*—Foley & Lardner

[57] ABSTRACT

In an electronic endoscope apparatus containing an objective optical system and a CCD sensor at the distal end thereof, the optical system and CCD sensor are moduled in an optical module tube. The optical module tube is first separately formed from the body of the distal end portion of the electronic scope. In the optical module tube, a focusing of the objective optical system is preadjusted with respect to the CCD sensor. Thereafter, the optical module tube containing the focus-adjusted optical objective optical system is assembled with the body of the distal end portion.

9 Claims, 4 Drawing Sheets

ELECTRONIC ENDOSCOPE APPARATUS INCLUDING EASY FOCUSING DISTAL END

BACKGROUND OF THE INVENTION

1. Field of the Invention

The present invention generally relates to an electronic endoscope apparatus. More specifically, the present invention is directed to an improved objective lens system employed in a non-bending distal end portion of an electronic endoscope apparatus.

2. Description of the Related Art

In a conventional electronic endoscope apparatus equipped with an electronic (endoscopic) scope having an objective optical system mounted on a non-bending distal end portion thereof, a focusing mechanism is directly screwed to this distal end portion and then fixed therein.

With such a focusing mechanism screwed to the non-bending distal end portion, there are drawbacks. The simple assembling of the distal end portion of the conventional electronic scope may not be as easy as first expected, and secondly the focusing thereof may be difficult. Furthermore, amount of projection of the objective (endoscope) lens beyond the distal end of the endoscope body can vary, depending upon the manufacturing conditions of the conventional electronic endoscope apparatuses, i.e., the fine adjustment states of the focusing.

If the surface projection amounts of the objective optical systems become irregular for each electronic scope, the cleaning fluid break of the scope cannot always be expected when the endoscopic examination is interrupted or completed and, then the electronic scope is cleaned with cleaning fluid.

The present invention has been made to solve the above-explained problems with a conventional electronic endoscope apparatus and, therefore, has as an object to provide an electronic endoscope apparatus equipped with an electronic scope on which such an objective optical system with easy focusing is mounted with easy assembling, whereby surface projection amounts of the objective lens do not become irregular every time during objective focusing.

SUMMARY OF THE INVENTION

These and other objects of the present invention are achieved by providing an electronic endoscope apparatus comprising an optical module tube 4 constructed of a moduled objective optical system 8. This optical module tube 4 is separately provided with a body 7 of a non-bending distal end portion 3 of an electronic scope 2.

BRIEF DESCRIPTION OF THE DRAWINGS

For a better understanding of the present invention, reference is made to the following description in conjunction with the accompanying drawings, in which.

DETAILED DESCRIPTION OF THE PREFERRED EMBODIMENTS

CONSTRUCTION OF FIRST ELECTRONIC SCOPE

Figure 1:
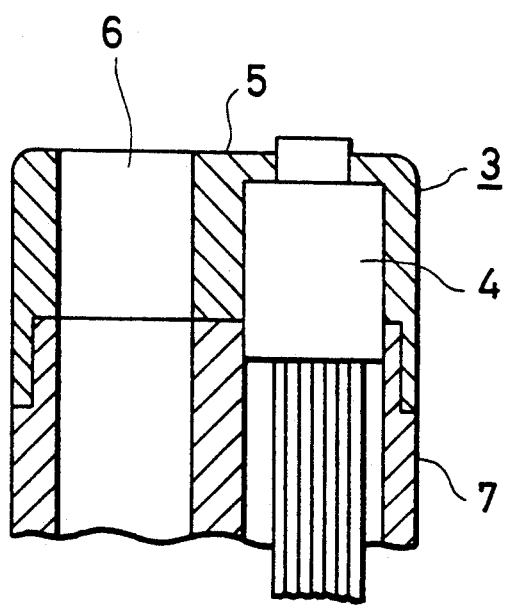
FIG. 1 is a fragmentary sectional view of an enlarged distal end portion employed in an electronic endoscope apparatus according to a first preferred embodiment of the present invention.
Figure 2:
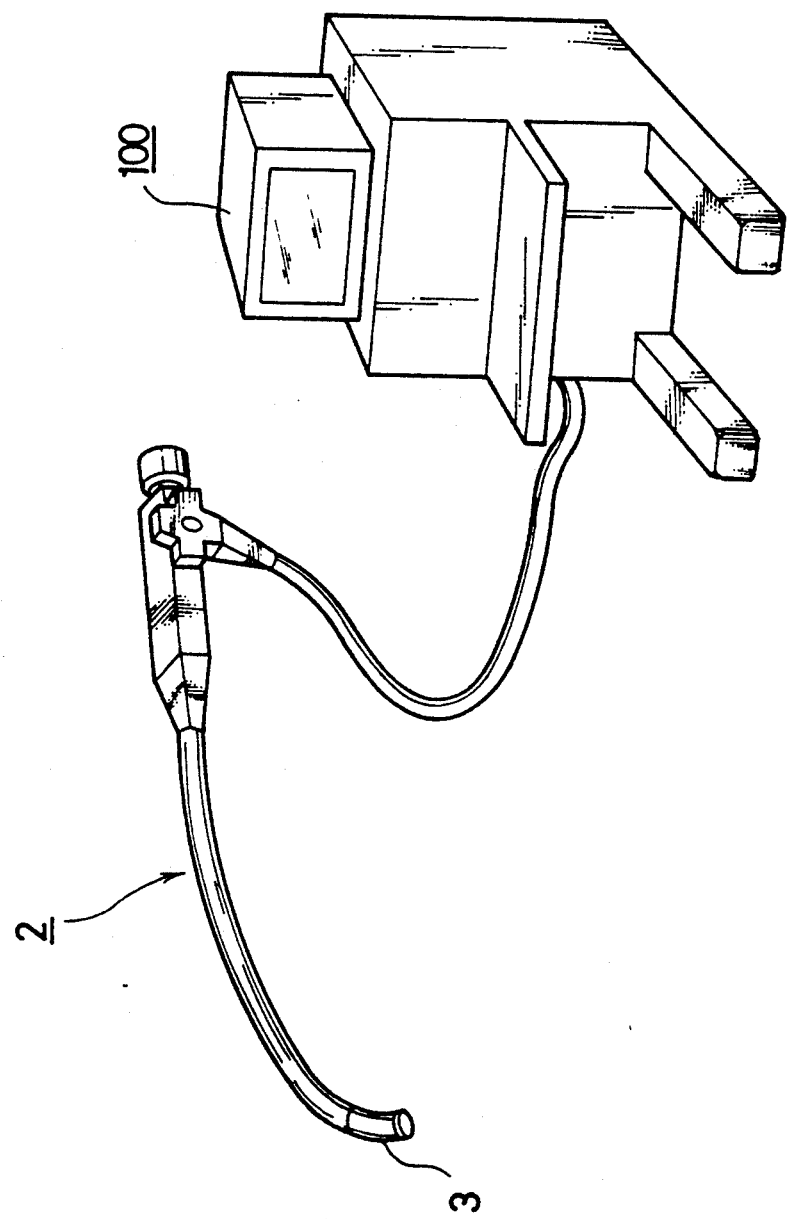
FIG. 2 is a perspective view of an overall arrangement of the electronic endoscope apparatus according to the first preferred embodiment.
Figure 3:
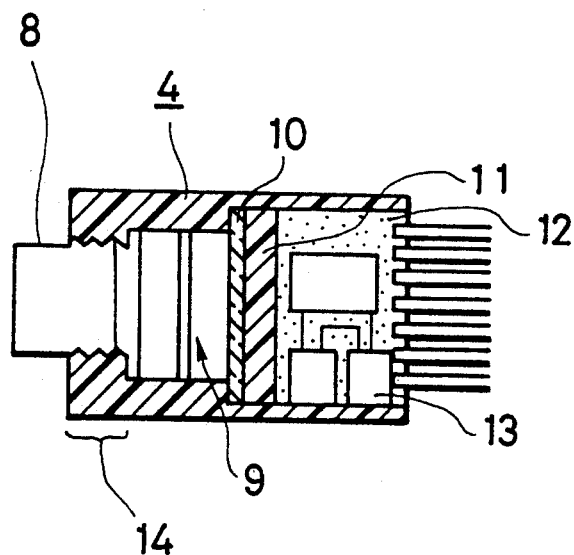
FIG. 3 is a sectional view of an optical module tube employed in the distal end portion shown in FIG. 1.

Referring now to FIGS. 1 to 3, a construction of an electronic scope employed in an electronic endoscope apparatus according to a first preferred embodiment of the present invention will be described.

FIG. 1 is a fragmentary sectional view of a non-bending distal end portion of an electronic (endoscopic) scope 2, of the first preferred embodiment, employed in an electronic endoscope apparatus 100. FIG. 2 is a perspective view of the electronic endoscope apparatus 100 equipped with the electronic scope 2, according to the first preferred embodiment. FIG. 3 is a sectional view of the optical module tube shown in FIG. 1.

As shown in FIGS. 1 and 2, with respect to the non-bending distal end portion 3 of the electronic scope 2, an optical module tube 4 is inserted into a tip cap 5. A forceps channel 6 is formed beside the optical module tube 4 and inside a body 7 of the distal end portion 3.

The optical module tube 4 is separately formed with respect to the body 7 of the distal end portion 3, which constitutes a feature of the present invention.

As represented in FIG. 3, this optical module tube 4 is so constructed that an objective optical system arranged by an optical lens (objective lens) system 8, an optical low-pass filter 9, a glass substrate 10, a solid-state imaging element (e.g., CCD) chip 11, a flexible printed circuit board (FRC) 12, and a chip component 13.

FOCUSING MECHANISM/POSITIONING OF OPTICAL MODULE TUBE

In the optical module tube 4 shown in FIG. 3, a screw groove (female thread) portion 14 is formed on a tube portion thereof to which the optical lens system 8 is mounted. Then, the focusing of this optical module tube 4 is realized by changing a screwing amount (distance) of the optical lens system 8 screwed into this screw groove portion 14 of the optical module tube 4.

A diameter of the optical low-pass filter 9 positioned between the optical lens system 8 and the CCD chip 11 is designed to be smaller than that of the CCD chip 11, and also to be slightly larger than that of the optical lens system 8, so that an easy positioning of this optical low-pass filter 9 may be realized.

The shape of this optical low-pass filter may be selected from either a square pole or a circular pole, preferably a square pole, because the signal reading directions of the CCD chip 11 are both the horizontal and vertical directions, i.e., square shape.

Figure 5:
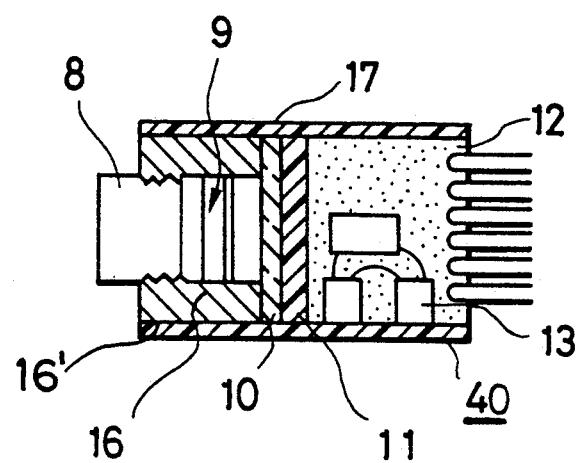
FIG. 5 is a sectional view of an optical module tube according to a second preferred embodiment of the present invention; and, FIG. 6 represents a cross-sectional view of an insulating cover employed in the second preferred embodiment.

On the other hand, the CCD chip 11 is positioned perpendicularly to an optical axis of this objective optical system 8. This CCD chip 11 is so designed that electrical conductivity is realized by an electrode (not shown in detail) patterned on a glass substrate 10. Since the CCD chip 11 is designed as above, it is required that the CCD chip 11 is electrically insulated from the metallic portion. This is because, in general, an electronic endoscope apparatus, specifically, an electronic endoscopic scope to be directly inserted into a body cavity of a patient has sufficient withstanding voltages, e.g., 500 to 1,500 Vpp, namely sufficient electrical insulation is required. In view of this electrical insulation, a housing of this optical module tube 4 is manufactured of an insulating material in accordance with the first preferred embodiment. Alternatively, the metallic portion's surface of the objective optical system moduled in the optical module tube 4 may be coated with an insulating material, for instance, by CVD (chemical vapor deposition) treatment. This coating is indicated by the numeral 16' (FIG. 5).

The chip components 13 such as resistors, diodes and capacitors, are provided on FPC 12 which is positioned within a space behind the CCD chip 11. As a result of the arrangement of this optical module tube 4, since the processes of the components are performed along a single direction and these components are assembled along this single direction, the construction and assembling becomes easier, as compared with those of the conventional endoscope apparatus.

ASSEMBLING OF OPTICAL MODULE TUBE WITH JIG

With employment of the above-described optical module tube 4, the focusing adjustment is carried out by changing the screwing amount (distance) of the optical lens system 8 into the screws groove portion 14 of the optical module tube 4 before this optical module tube 4 is attached to the non-bending distal end portion 3 of the electronic endoscopic scope 2, and also the surface projection amount of the objective lens employed in the optical lens system 8 may be preset to a constant (preselected) value.

As a result of such a featured arrangement of the optical module tube 4, the following easy assembling process may be achieved.

Figure 4:
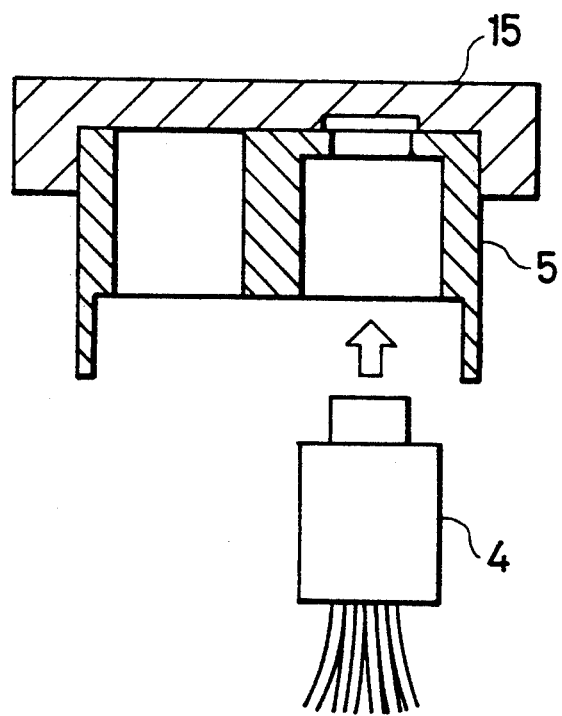
FIG. 4 illustrates an assembling state when the optical module tube is assembled with the distal end portion according to the first preferred embodiment.

That is, according to the first preferred embodiment, the optical module tube 4 may be simply assembled with the non-bending distal end portion 3 of the electronic scope 2 under such a condition that a cap assembling jig 15 is engaged with the tip cap 5, as illustrated in FIG. 4. In addition to the above-described advantage of the first preferred embodiment, there is neither variation, nor fluctuation in the surface projection amount of the optical lens system 8 from the tip cap 5. Also, since the focusing process of the optical module tube 4 has been accomplished prior to finally assembling the optical module tube 4 with the tip cap 5 of the electronic scope 2, no optical adjustment is required with respect to the surface projection amount of the optical lens.

The features of the first preferred embodiment are summarized. The focusing adjustment of the optical lens system 8 becomes very simple and also the non-bending distal end portion of the electronic scope may be readily assembled. Furthermore, irregularity of the surface projection amount of the optical lens system with respect to the tip cap 5 may be avoided.

CONSTRUCTION OF SECOND ELECTRONIC SCOPE

In FIG. 5, there is shown a sectional view of an optical module tube 40 according to a second preferred embodiment of the present invention. This optical module tube 40 is fabricated so that an objective optical system constructed of the optical lens system 8, optical low-pass filter 9, glass substrate 10, CCD chip 11, FPC (flexible printed circuit board) 12, and chip component 13 is moduled under the a condition that both the optical lens system 8 and optical low-pass filter 9 are contained in a holder 16, and also, surroundings of the moduled objective optical system are covered with an electrically insulating cover 17.

Figure 6:
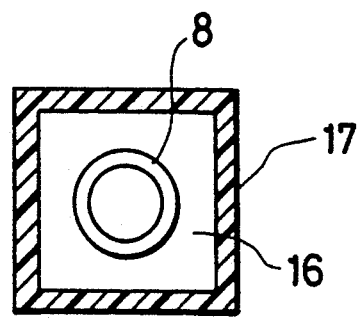

As previously described, since the optical module tube 4 is constructed of two separate configurations, i.e., the holder 16 and the electrically insulating cover 17, this holder 16 for positioning the optical lens system 8 and optical low-pass filter 9, which requires the specific machining such as thread cutting, may be made of a metal material. As a consequence, although the metal holder per se has no electric insulating characteristic, the metal holder may be readily mechanically-processed. Moreover, a square pole may be employed as the shape of the insulating cover 17, as shown in FIG. 6, which is also simply mechanically-processed, so that this insulating cover 17 may be made of glass or a ceramic.

In accordance with the optical module tube 40 of the second preferred embodiment, there are the following particular advantages. First, since the insulating cover can be simply processed, the manufacturing cost of the optical module tube 40 is considerably lowered, as compared with that of the first preferred embodiment. Secondly, the resultant withstanding voltage achieved by the second optical module tube 40 is rather higher than that of the first optical module tube 4.

As previously described in detail, in accordance with the electronic endoscope apparatus of the present invention, the objective optical system is previously manufactured as a module to thereby construct the optical module tube independently from the body of the non-bending distal end portion. Before the optical module tube is assembled with the body of the distal end portion in order to construct a finally desirable distal end portion of the electronic scope, the focus adjustment of the optical module tube has been completed with a simple adjusting work. Moreover, such an optical module tube can be easily assembled with the body of the distal end portion, and also no irregularity exists in the surface projection amount of the objective lens mounted in the optical module tube from the tip portion thereof. When the housing of the optical module tube is fabricated by separately employing the holder and the electrically insulating cover, both the mechanical process and the withstand voltage can be further improved.

What is claimed is:

1. An electronic endoscope apparatus comprising:
an electronic endoscope means having a non-bending distal end portion, to be inserted into a cavity of a biological body under medical examination; and
an optical module tube means, including at least an objective optical system, having an objective lens, and an image sensor for electronically imaging the body cavity of the biological body through the objective optical system, a housing mounted on the distal end of the endoscope means for receiving and retaining the tube means, said optical module tube means being separately and exteriorly assembled outside of said housing, the objective lens contained by a lens holder within the module tube means and protruding through both the flat distal end of the module tube means in the direction of the distal end of the endoscope and the distal end of the housing a distance determined by an adjustment jig, the amount of protrusion being adjusted by rotation of the lens holder with respect to the module tube means, the lens holder and module tube means having, respectively, male and female threading for carrying out such adjustment.

2. An electronic endoscope apparatus comprising:
an electronic endoscope means having a non-bending distal end portion for insertion into a cavity of a biological body;
an optical module tube including at least an objective optical lens, a lens holder and a charge coupled device, said charge coupled device being larger than said optical lens; and
a housing mounted at the distal end of the endoscope means for receiving and retaining the module tube, wherein the module tube is assembled outside of the housing for insertion upon assembly into the housing, the lens holder protruding both through a flat distal end of the module tube and the distal end of the housing, the amount of protrusion being adjusted by rotation of the lens holder with respect to the module tube, the lens holder and module tube having, respectively, male and female threading for carrying out an adjustment.

3. An electronic endoscope apparatus as claimed in claim 2, wherein said optical module tube is made of an electrically insulating material.

4. An electronic endoscope apparatus as claimed in claim 2, wherein said optical module tube is coated with an electrically insulating film.

5. An electronic endoscope apparatus as claimed in claim 2, wherein said optical module tube further includes:
an optical low-pass filter for filtering imaging light derived from the objective optical system to produce filtered imaging light to be supplied to the image sensor.

6. An electronic endoscope apparatus as claimed in claim 2, further including;
a cavity at the module tube distal end, the cavity including said female threading, said lens holder having a portion on its outer surface with said male threading for adjusting the lens holder a selected distance into the cavity, the objective lens being focused by the amount of threading thereof.

7. An electronic endoscope apparatus as claimed in claim 2, wherein said optical module tube has a circular shape, as viewed in a cross-sectional plane thereof.

8. An electronic endoscope apparatus as claimed in claim 2, wherein said optical module tube has a rectangular shape, as viewed in a cross-sectional plane thereof.

9. An electronic endoscope apparatus as claimed in claim 2, further including an electrically insulating cover surrounding said optical module tube and said lens holder.

* * * * *